Figure 1:
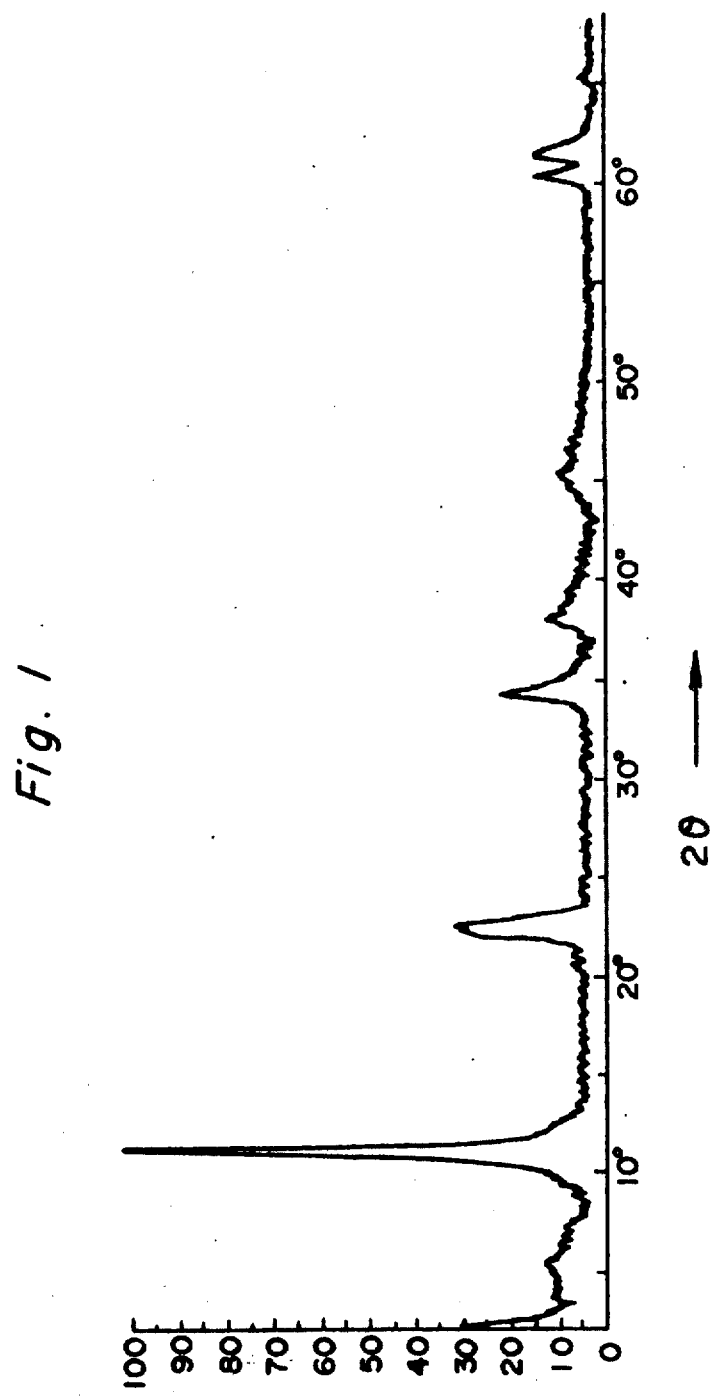

United States Patent [19]

Miyata et al.

[11] 3,980,685
[45] Sept. 14, 1976

[54] MAGNESIUM-ALUMINUM CONTAINING COMPLEXES OF ORGANIC ANIONS OF CENTRAL NERVOUS SYSTEM AFFECTING COMPOUNDS

[75] Inventors: Shigeo Miyata; Michiko Takata; Akira Okada, all of Takamatsu, Japan

[73] Assignee: Kyowa Chemical Industry Co., Ltd., Tokyo, Japan

[22] Filed: Sept. 30, 1974

[21] Appl. No.: 510,553

Related U.S. Application Data

[63] Continuation-in-part of Ser. No. 499,920, Aug. 23, 1974, abandoned, which is a continuation of Ser. No. 241,009, April 4, 1972, abandoned.

[52] U.S. Cl. .......................... 260/448 R; 260/270 B; 260/326.13 R; 260/448 B; 424/228; 424/230; 424/258; 424/274; 424/317; 424/319
[51] Int. Cl.$^2$............................................ C07F 5/06
[58] Field of Search ..................... 260/448 R, 448 B

[56] References Cited
UNITED STATES PATENTS

| | | | |
|---|---|---|---|
| 2,874,177 | 2/1959 | Hayano | 260/448 B |
| 2,918,485 | 12/1959 | Schenk et al. | 260/448 B |
| 3,100,787 | 8/1963 | Staib | 260/448 B |
| 3,352,893 | 11/1967 | Holbert et al. | 260/448 B |
| 3,391,176 | 7/1968 | Grossmith | 260/448 B |
| 3,409,655 | 11/1968 | Seki et al. | 260/448 R |
| 3,553,316 | 1/1971 | Rubino | 260/448 B |
| 3,573,006 | 3/1971 | Shih et al. | 260/448 B X |

*Primary Examiner*—Helen M. S. Sneed
*Attorney, Agent, or Firm*—Sherman & Shalloway

[57] ABSTRACT

A compound having a composition of the following formula:

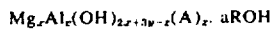

$Mg_xAl_x(OH)_{2x+3y-z}(A)_z \cdot aROH$ wherein A is a member selected from the group consisting of
  a. a mono- or bivalent anion of a central nervous system medicament having a functional group selected from the class consisting of carboxyl, hydroxy and sulfonic groups, and
  b. a combination of said mono- or bivalent anions of a central nervous system medicament and not more than 50 mol %, based on the total anions, of an ion selected from the group consisting of halogen, nitrate, carbonate and sulfate ions,
R is a member of the group consisting of hydrogen and ethyl, and $x$, $y$, $z$ and $a$ are each a positive number satisfying the following relationships:

$$1/4 < x/y < 8$$
$$1/20 < \frac{z}{x+y} < 2/7$$

and $$0.25 < \frac{a}{x+y} < 1.$$

and a process for the preparation of said compounds.

4 Claims, 9 Drawing Figures

MAGNESIUM-ALUMINUM CONTAINING COMPLEXES OF ORGANIC ANIONS OF CENTRAL NERVOUS SYSTEM AFFECTING COMPOUNDS

This is a continuation-in-part of Ser. No. 499,920 filed Aug. 23, 1974, which in turn is a continuation of Ser. No. 241,009, filed Apr. 4, 1972, both of which are now abandoned.

This invention relates to a new compound containing an organic anion of a central nervous system medicament and to a process for the preparation of same. More specifically, the invention relates to a new complex which is valuable for use as an antipyretic, analgesic, antirheumatic and antiflammatory agent.

According to this invention, there is provided a compound having a composition of the following formula:

$$Mg_xAl_y(OH)_{2x+3y-z}\cdot Az\cdot aROH \quad (1)$$

wherein A is
a. a mono- or bivalent anion of a central nervous system medicament having a functional group selected from the class consisting of the carboxyl, hydroxyl and sulfonic groups, or
b. a combination of such mono- or bi-valent anions of a central nervous system medicament and not more than 50 mol %, based on the total anions, of an ion selected from the group consisting of halogen, nitrate, carbonate and sulfate ions, R is a member of the group consisting of hydrogen and ethyl, and $x$, $y$, $z$ and $a$ are each a positive number satisfying the following relationships:

$$1/4 \leq x/y \leq 8$$

$$1/20 < z/x+y < 2/7$$

$$0.25 \leq a/x+y \leq 1;$$

and having an X-ray diffraction pattern substantially identical to that indicated below.

| dA | hkl |
|---|---|
| 7.62 ~ 21.02 | 003 |
| 3.93 ~ 9.40 | 006 |
| 2.11 ~ 6.91 | 102 |
| 2.34 ± 0.5 | 105 |
| 2.00 ± 0.5 | 108 |
| 1.53 ± 0.05 | 110 |
| 1.50 ± 0.05 | 113 |

Numerous organic compounds having as the functional group the carboxyl, hydroxyl or sulfonic groups are already known as being central nervous system medicaments, and especially as antipyretics, analgesics, antirheumatics and antiflammatory agents. In most cases, these medicaments are administered to the patient orally. Of these medicaments, those which are typical are given in Table 1, below. In the table, the name, the chemical formula or chemical name, dosage, the disease for which the medicament is efficacious, and ill effects and diseases for which the medicament is contraindicated are shown.

Table 1

| Name of Medicine | Chemical Formula | Dosage | Efficacious for | Ill Effects | Contra-indication | Other Information |
|---|---|---|---|---|---|---|
| Indomethacin | CH₃·O-[indole with CH₂·COOH, CH₃, C=O, p-Cl-phenyl] | initially 0.025–0.05 weekly increase (0.025g) 0.1–0.15 g/day | counteraction of chronic articular rheumatic inflammation | loss of appetite, stomach pain, nausea, diarrhea, constipation | patients suffering from stomach or duodenal ulcer. | alkaline side instability |
| Flufenamic acid | [COOH-phenyl-NH-phenyl-CF₃] | 0.2–0.6 g/day | bone arthritis | gastro-intestinal troubles | " | bitter |
| Mefenamic acid | [COOH-phenyl-NH-phenyl(CH₃)(CH₃)] | 0.5–1 g/day | pain | " | " | odorless |
| Ibuprofen | (CH₃)₂CH–CH₂–[phenyl]–CH(CH₃)–COOH | 0.3–0.9 g/day | articular rheumatism | heartburn, nausea | — | distinctive odor and taste |
| Ibufenac | (CH₃)₂CH–CH₂–[phenyl]–CH₂·COOH | as analgesic and antiphlogistic 0.75–2.0 g/day, as antiphlogistic | pain killing fever alleviation | gastro-intestinal troubles | — | pungent odor |

Table 1-continued

| Name of Medicine | Chemical Formula | Dosage | Efficacious for | Ill Effects | Contra-indication | Other Information |
|---|---|---|---|---|---|---|
| Probenecid | HOOC—C₆H₄—SO₂N(CH₂CH₂CH₃)₂ p-(di-n-propylsulfonyl-benzoic acid) | 1.5g/day initially for one week 0.25–1.0 g/day | gout | " | — | — |
| Chinophenum | (structure: quinoline with COOH and phenyl) | 2.0g/day | neuralgia | loss of appetite, vomiting | gastric ulcer | odorless |
| Sulpyrin | NaO₃S.CH₂—(pyrazolone structure with N—C=C—CH₃, O=C, N—CH₃, N-phenyl) | orally 1.0g/day maximum 3.0 g/day | " | eruptions | — | " |
| Salicylsalicylic acid | (structure: two salicyl rings joined by CO·O, with OH and COOH) | 1.5g/day | common cold | gastro-intestinal troubles | — | odorless bitter |
| Salicylic acid | (structure: benzene ring with COOH and OH) | — | — | " | | distinctive odor and taste |

We have succeeded in the synthesis of a new complex which contains as its effective constituent the anion of a central nervous system medicament such as shown in the foregoing Table 1.

The new complex of the present invention is a compound having a composition such as shown by the foregoing generic formula (1) and a layered crystalline structure such as shown by the aforesaid X-ray diffraction pattern. The complex, which is the base of the compositions of the instant invention, has the formula $$Mg_6Al_2(OH)_{16} \cdot A_n \cdot a'ROH \qquad (2)$$

wherein A and R are as hereinbefore defined, $n$ is 2 when A is a monovalent anion and 1 when A is a bivalent anion, and $a'$ is a number from 2.5 to 6. A compound having a composition and crystalline structure analogous to the compound is represented by the foregoing formula (2), is known as hydrotalcite and has the formula $$Mg_6Al_2(OH)_{16} \cdot CO_3 \cdot 4H_2O \qquad (3).$$

The new complex of the invention can be regarded as being a compound in which the carbonate ion of hydrotalcite has been substituted by a specific organic anion. However, it must be noted that the new complex of this invention cannot be synthesized by an ion-exchange method wherein the carbonate ion of hydrotalcite is replaced by an organic anion.

The mono- or bivalent anion in the foregoing formulas (1) and (2) which may be utilized are those mono- or bivalent anions of organic compounds which have as their functional group a member selected from the group consisting of carboxyl, hydroxyl and sulfonic groups and which can be used as a central nervous system medicament, and particularly as an antipyretic, analgesic, antirheumatic and antiflammatory agent. Such organic compounds are well known by those skilled in the art, and any of such known compounds can be used in the instant invention.

The anions of the compounds such as those shown in Table 1 are conveniently useable as the mono- or bivalent anion in the invention. Included are, for example:

a. The case wherein anion A is an anion of a compound of the formula

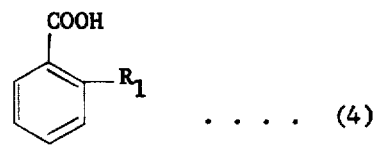

.... (4)

wherein R₁ is either a hydroxyl, acyloxy, e.g., acetyloxy, salicyloxy, 3-trifluoromethylphenylamino, or 2,3-dimethylphenylamino group.

b. The case wherein anion A is an anion of a compound of the formula

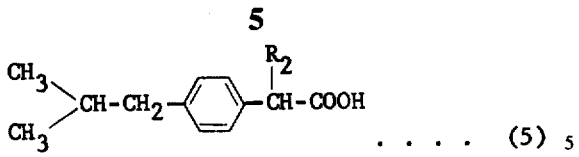

. . . . (5)

wherein $R_2$ is either a hydrogen atom or methyl group.

c. The case wherein anion A is the anion of p-(di-n-propylsulfanyl)-benzoic acid.
d. The case wherein anion A is the anion of 1-(p-chlorobenzoyl)-5-methoxy-2-methylindole-3-acetic acid.
e. The case wherein anion A is the anion of 2-phenyl-4-carboxy-quinoline.

While it is preferred that the mono- or bivalent anions A in the new complex of this invention are all anions of the abovementioned effective constituents, the halogen ions, e.g., $Cl^-$, $Br^-$ and $I^-$, the nitrate ion, the carbonate ion or the sulfate ion may also be present up to no more than 50 mol % of the anion A.

In the generic formula (1), it is preferred that $x$ is a number from 3 to 10 when $y$ is 2; $z$ is from 1.5 to 2.5, when A is a monovalent anion, and 0.75 to 1.25, when A is a bivalent anion; and $a$ is a number from 2.5 to 6.

The new complex of the invention possesses the following characteristics.

In the invention complex, a mixed crystal of Mg and Al is formed in a given range of Mg and Al, i.e., where $1/4 \leq x/y \leq 8$. This can be understood from the fact that when the compound of the invention is synthesized with varied proportions of Mg and Al and the resulting products are analyzed by means of the powder X-ray diffraction method, the lattice constant [(006) surface] and the mole ratio of Mg/Mg+Al are proportionally related and hence in conformance with Vegard's law.

Vegard's law states that the following relationship holds when a mixed crystal of A and B is formed, that is, $$d = k_1 d_1 + k_2 d_2$$

where $d$ is the lattice constant, $k_1$ and $k_2$ are constants, and $d_1$ and $d_2$ are the lattice constants individually possessed by A and B.

The invention compound is a crystalline substance of layered structure and its refractive index in the case of any of its compositions is in the range of 1.4 – 1.7. Further, it is insoluble in water and organic solvents, but starts to dissolve in acids at from usually about pH 4. While it is generally insoluble in alkalies it starts to dissolve therein when the pH becomes 13 or more. This property of the compound of this invention, i.e., its insolubility in alkalies, is a marked characteristic thereof, along with the fact that the alkaline content of the resulting compound is as small as 0.01 to 0.001 %.

The size of the crystals of the compound of this invention is usually distributed in the range of 60 – 200 A at room temperature and normal atmospheric pressure. This crystal size can be enlarged as desired by a hydrothermal treatment. The crystal structure is made up of a layer consisting of 0.1 bonds of either $Mg(OH)_2$, or $Mg(OH)_2$ and $Al(OH)_3$, and an intermediate layer consisting of coordinate anions and water or ethanol molecules, which layers are serially joined together. Both $Mg(OH)_2$ and $Al(OH)_3$ form an octahedral layer of six coordinates.

A coordinate anion A is present substantially perpendicular to the octahedral layers and joins two of the octahedral layers together. Thus, the distance between the layers varies in accordance with the size of the ligand and, in addition, the amount of the interlayer crystal water also varies. As a general rule, in proportion as the size of the intermediate layer formed by the coordinate anion becomes about n-fold of 3.2 A, the interlayer crystal water increases n-fold.

The invention compound, in consequence of its being a layered crystalline structure, is more heat stable than $Mg(OH)_2$, $Al(OH)_3$ and A alone by more than 100°C.

The invention compound can very readily be distinguished and identified from the other compounds by means of X-ray diffraction analysis. The powder X-ray diffraction pattern of the invention compound is shown in Table 1.

Table 1

| dA | Measurement conditions: Cu-Kα ray, Ni filter. | |
|---|---|---|
|  | hkl | I/Io |
| 7.62 ~ 21.02 | 003 | 100 |
| 3.93 ~ 9.40 | 006 | 40 |
| 2.11 ~ 6.91 | 102 | 20 |
| 2.34 ± 0.5 | 105 | 21 |
| 2.00 ± 0.5 | 108 | 22 |
| 1.53 ± 0.05 | 110 | 9 |
| 1.50 ± 0.05 | 113 | 11 |

Note:
dA ...... Spacing
I/Io ...... Relative intensity
hkl ...... Miller indices The compound of the present invention is hexagonal, rhombohedral or a mixture thereof. In each case, the lattice constant may be expressed as a hexagonal system where $a_o$ (lattice constant) is distributed in 3.03 – 3.10 A (rhombohedral)
    $c_o$ (lattice constant) is distributed in 23.88 – 63.06 A. or 15.92 – 42.04 A (hexagonal)

As is apparent from the above $a_o$ is almost invariable. Moreover, the lattice constant of $Mg(OH)_2$ is a bit smaller than 3.147 A, which fact originates from substitution of Mg of $Mg(OH)_2$ by Al.

Along with the increase of Al in proportion to Mg, therefore, $a_o$ decreases from 3.10 A to 3.03 A. This can be proved by Vegard's rule described above. Accordingly, the compounds of the present invention have in common that $d_{110}$ varies only very slightly.

On the other hand, $c_o$ depends principally on the size of the anion. Namely, the construction of the compounds of the present invention comprises an analogous layer of Brucite (cadmium iodide type) which charges positive by substitution of Mg by Al, positive charge, and an intermediate layer (comprising anion and water) which is required to maintain electrical neutrality. Generally, such a construction tends to be superlattice construction. Accordingly, the total thickness of the Brucite analogous layer and the intermediate layer is substantially equal to the total of $c_0 = 4.760$ A of $Mg(OH)_2$ plus the size of organic anion, which is the thickness of the basic layer.

The $c_o$ of the compound of the present invention is three times (rhombohedral) or two times (hexagonal) the thickness of the basic layer. In most cases, $c_o$ has triple thickness and primarily occupies the resulting product.

Accordingly, $c_o$ varies in a wide range in accordance with the size of the anion, but $a_o$ has a valency approximate to $Mg(OH)_2$.

Examples of the indexed samples of the present invention are shown in the following paragraph.

Characteristic faces of the compounds of the present invention are as follows: (003) (006) (102) (105) (108) (110) (113).

Of these faces, X-ray diffraction patterns of (003), (006), (110) and (113) are symmetrical as well as sharp, whereas the faces of (102), (105) and (108) are tailing to a high degree and broad. These features are peculiar to biostromal compounds, specifically to clay type minerals.

Of course, it will be understood by those skilled in the art that the relative intensity varies naturally to a considerable extent in accordance with types of anions incorporated.

The hereinbefore described new complex of the instant invention is prepared by the following method.

According to the present invention, there is provided a process for producing a compound of the formula $$Mg_xAl_y(OH)_{2x+3y-z}A_z \cdot aH_2O$$

wherein $x$, $y$, $z$, $A$ and $a$ are each as above defined, which comprises reacting in either water or alcohol at a pH of at least 8.0 a. a compound of the formula $$MgX_2 \qquad (6)$$

wherein X is halogen or a nitric acid, b. an alkali metal salt of aluminic acid or a compound of the formula $$AlY_3 \qquad (7)$$

wherein Y is halogen, a nitric acid group or a lower alkoxy group, and c. a compound of the formula $$AM \qquad (8)$$

wherein M is hydrogen or an alkali metal and A is as above defined.

Magnesium chloride, magnesium bromide, magnesium iodide and magnesium nitrate can be used as the foregoing compound of formula (6). On the other hand, aluminum chloride, aluminum bromide, aluminum nitrate, aluminum ethoxide and aluminum isopropoxide can be used as the compound of formula (7), while as the starting aluminum material the alkali metal aluminates such as potassium and sodium aluminates may be used.

When in this case the carbonate ion or sulfate ion is introduced into the aforesaid compound of formula (1) in an amount of not more than 50 mol % of the anion A, a magnesium salt such as magnesium sulfate and basic magnesium carbonate or aluminum sulfate, e.g., an alkali carbonate-aluminum hydroxide complex such as $Al(OH)_3 \cdot Na_2CO_3$, may be used conjointly with the aforesaid starting magnesium or aluminum material.

According to the invention, the aforesaid compounds of formula (8), e.g., the compounds shown in Table 1, above, can be used, as such, or in the form of their alkali metal salts.

Instead of using the magnesium compound of formula (6) and the organic compound of formula (8) separately, it is, of course, possible to use a magnesium salt of an organic anion A as the starting material. In this case, however, it is necessary that the magnesium salt of an organic anion A be one which fully dissolves in the reaction medium.

It is important that the reaction of this invention be carried out in either water or a lower alcohol such as ethanol and at a pH of at least 8, and preferably at least 9. The choice of these solvents is made after taking into account the solubility of the starting materials in these solvents. It is preferred to choose a solvent whose solvent power for the starting material is great. For raising the pH to the conditions required above, hydroxides of alkali metals or ammonia (or ammonium hydroxide) are added to the reaction system as the source for supplying $OH^-$.

In practicing the process of the present invention, it is important that the reaction be carried out under conditions in which substantially no carbonate ions are present in the reaction system, because where the carbonate ions are present in the reaction system, they become preferentially incorporated in the crystalline structure as compared with the organic anions. Thus, in practicing the process of this invention, consideration must be given to such matters as using water wherein carbonic acid has been removed and purging the interior of the reaction vessel with nitrogen. For similar reasons, care must be exercised to ensure that the reaction system is not adulterated by other bivalent inorganic ions, e.g., sulfate ions. However, where the carbonate ions or sulfate ions are to be introduced in an amount of above 50 mol % of the anion A in the foregoing compound of formula (1), the presence in the reaction system of the carbonate or sulfate ions in an amount in the foregoing range is, of course, permissible.

While no particular restrictions are imposed on the proportion in which the starting materials are used, the starting magnesium and aluminum materials are best employed in a ratio such that $y$ mols of $Al^{3+}$ are used per $x$ mols of $Mg^{2+}$. Again, the presence of the organic anion $A$ in a ratio such as to provide at least $z$ mols per $y$ mols of $Al^{3+}$ is sufficient.

The other reaction conditions are optional and are not restricted. The reaction can be carried out, for instance, at a temperature ranging between room temperature and 100°C. and a pressure ranging between normal atmospheric pressure and about 10 atmospheres.

Now, when an organic compound having both a carboxyl group and a phenolic hydroxyl group, such as salicylic acid, is used in the present invention at a pH of less than 13.7, for example, a pH of 10, it acts as a monovalent anion, i.e.,

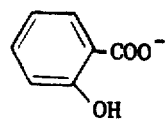

On the other hand, at a pH of 13.7 or more, it acts as a bivalent anion, i.e.,

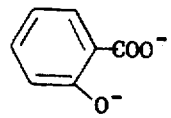

Thus, in accordance with the invention, salicylic acid can be incorporated in the crystalline structure as either a monovalent anion or a bivalent anion.

According to the invention, by carrying out the reaction under these conditions, the compound of formula (1) is formed as a precipitate. Therefore, the resulting compound may be recovered by an optional solid-liquid separation operation, followed by washing, if necessary, in water and drying.

The new complex obtained by the invention process can be submitted to various after-treatments, as required. For instance, these compounds can be given a hydrothermal treatment in water of 100° to 150°C. and, if necessary, under pressure.

Furthermore, when inorganic monovalent anion, e.g., halogen ions or nitrate ions, are contained in the resulting compound, the inorganic monovalent anions may be removed by contacting the resulting compound with an aqueous solution of the aforesaid compound of formula (8). This ion-exchange treatment can be carried out either by packing the resulting compound in a column and introducing the aforesaid aqueous solution into the column or by suspending the resulting compound in the aforesaid aqueous solution.

The new complex of the invention is valuable for use as a central nervous system medicament, and especially as an antipyretic, analgesic, antirheumatic and antiflammatory agent. It is administered to the patients orally in dosages such that the effective constituent, i.e., the organic anions, contained in the compound is administered in a dosage comparable to that customarily used, e.g., the dosages shown in Table 1. For instance, Table 2, below, shows several examples of the dosages in which the new compounds of the invention are to be administered.

Table 2

| Name of Substance | Dosage (g/day) |
|---|---|
| $Mg_6Al_2(OH)_{16}$(monovalent anion of Chinophenum)$_2$.5.1H$_2$O | 3.0 |
| $Mg_6Al_2(OH)_{16}$(monovalent anion of Sulpyrin)$_2$.4H$_2$O | 1.5 |
| $Mg_6Al_2(OH)_{16}$(monovalent anion of Salicylsalicylic acid)$_2$.3.1H$_2$O | 2.2 |
| $Mg_6Al_2(OH)_{16}$(monovalent anion of Ibuprofen)$_{2.5}$.5.3H$_2$O | 0.6 – 2.0 |
| $Mg_6Al_2(OH)_{16}$(monovalent anion of Ibufenac)$_2$.5.2H$_2$O | 1.8 – 4.5 |
| $Mg_6Al_2(OH)_{16}$(monovalent anion of Mefenamic acid)$_2$.4.8H$_2$O | 1 – 2 |
| $Mg_6Al_2(OH)_{16}$(monovalent anion of Flufenamic acid)$_2$.2.7H$_2$O | 0.4 – 0.8 |
| $Mg_{4.3}Al_2(OH)_{13}$(monovalent anion of Indomethacin)$_{1.6}$.2H$_2$O | 0.04 – 0.09 |
| $Mg_6Al_2(OH)_{16}$ 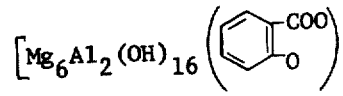 .3.8H$_2$O | 5 – 15 |

Table 2-continued

| Name of Substance | Dosage (g/day) |
|---|---|
| $Mg_6Al_2(OH)_{16}$ 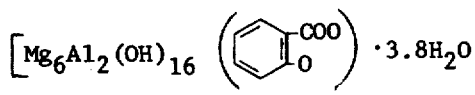 .4.2H$_2$O | 3.5 – 10 |

Figure 5:
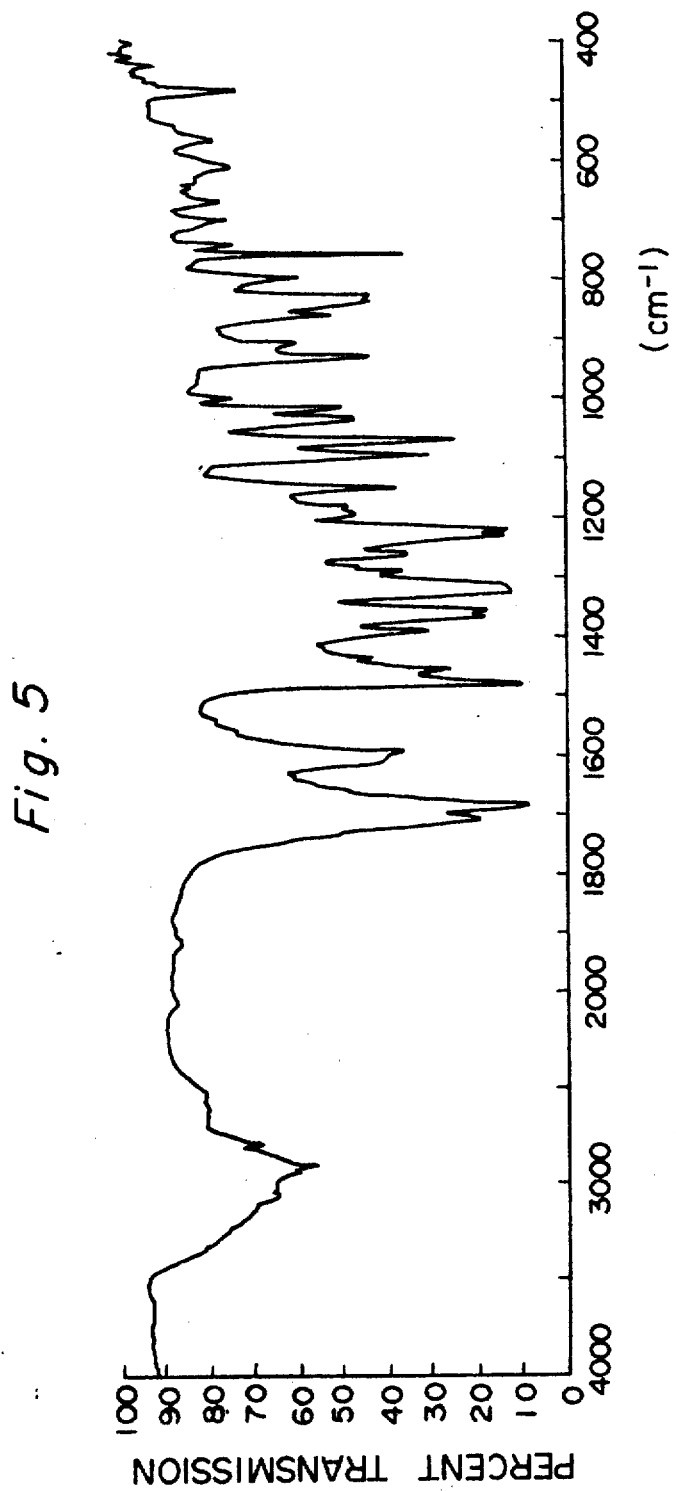
Figure 6:
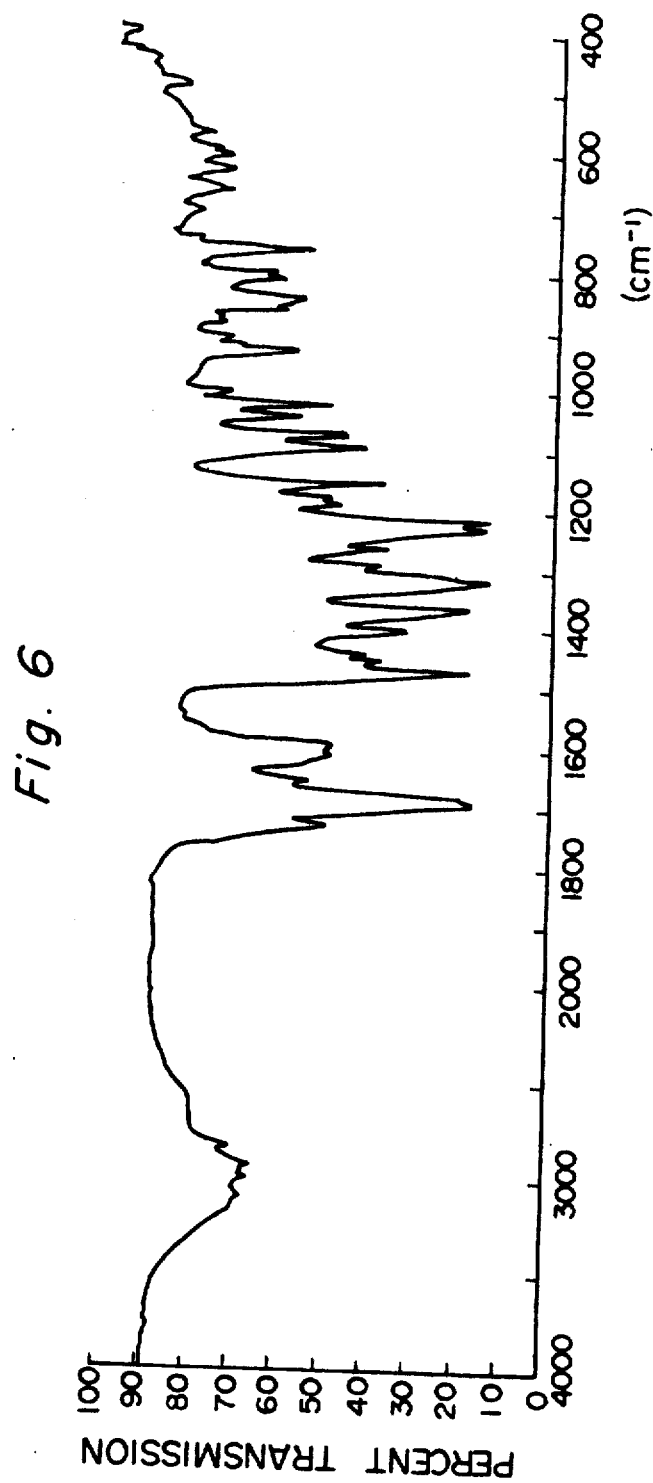

In the new complex of the invention, the organic anion, the medicinally effective constituent, is incorporated in the layered crystalline structure and is stable. That is, although the effective constituent is reacted with the magnesium and aluminum components in the new complex of the invention, the effective constituent is incorporated intact in the crystalline structure in its anion form. This fact can be readily appreciated, as shown in FIGS. 5 and 6, from the fact that the infrared absorption of the organic substance obtained by decomposing [$Mg_{4.3}Al_2(OH)_{13}$(monovalent anion of Indomethacin)$_{1.5}$($NO_3^-$)$_{0.1}$.2.3H$_2$O], a new compound of the invention, with dilute hydrochloric acid (1N) followed by extraction with chloroform coincides nearly perfectly with the infrared absorption spectrum of Indomethacin.

Further, since the new compound of the invention has a layered crystalline structure, it is stable both thermally and chemically. For instance, the new invention complex $$\left[Mg_6Al_2(OH)_{16}\left(\begin{array}{c}\text{COO}\\\text{O}\end{array}\right)\right]$$

decomposes at 420°C. This is far superior to that of salicylic acid whose decomposition temperature is 200°C. Moreover, the invention complex is exceedingly stable to ultraviolet rays.

Figure 4:
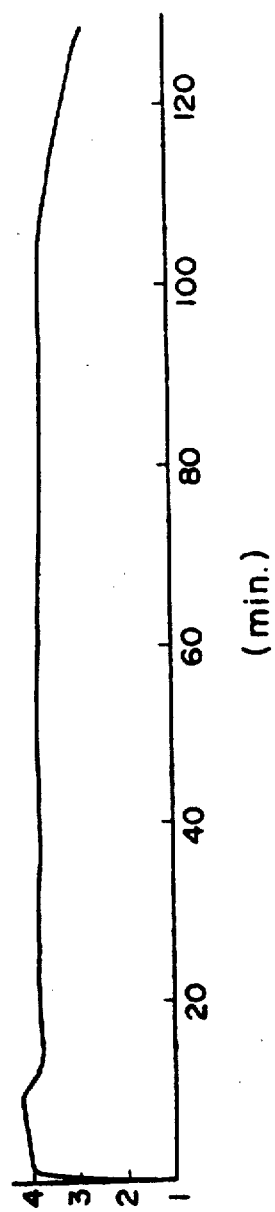

In addition, the new complex of the invention has the remarkable property in that it possesses the activities as an analgesic, antipyretic and antiflammatory agent, on the one hand, as well as that of an antacid preparation on the other. For instance, when the complex $$\left[Mg_6Al_2(OH)_{16}\left(\begin{array}{c}\text{COO}\\\text{O}\end{array}\right)\right] \cdot 3.8H_2O$$

of Example IV is added to an artificial gastric juice, the Fuch's curve is as shown in FIG. 4. Thus, it can be appreciated from this that the invention complex possesses properties as an antacid preparation having excellent properties such as quick activity, good maximum pH and long lasting activity. Furthermore, the new complex of the invention possesses, as such, good tablet formability, as can be readily seen from the results given in Table 3.

Table 3

| | THE COMPRESSIVE STRENGTH OF THE TABLETS* | | | | | |
|---|---|---|---|---|---|---|
| | Compressive Pressure (kg/cm²) | | | | | |
| Sample | 318 | 636 | 955 | 1274 | 1911 | 2548 |
| Alumina gel hydroxide | 2.4 | 6.0 | 11.2 | 16.8 | >25 | >25 |
| Crystallized lactose | 0 | 0 | 0.9 | 1.8 | 2.8 | 5.8 |
| Crystallized cellulose | 12.3 | 19.8 | >25 | >25 | >25 | >25 |
| Product of | 11.6 | >25 | >25 | >25 | >25 | >25 |

Table 3-continued

THE COMPRESSIVE STRENGTH OF THE TABLETS*

| Sample | Compressive Pressure (kg/cm²) | | | | | |
|---|---|---|---|---|---|---|
| | 318 | 636 | 955 | 1274 | 1911 | 2548 |
| Example I | | | | | | |
| Product of Example II | 11.2 | >25 | >25 | >25 | >25 | >25 |
| Product of Example III | 14.7 | >25 | >25 | >25 | >25 | >25 |
| Product of Example IV | 13.9 | >25 | >25 | >25 | >25 | >25 |
| Product of Example V | 12.5 | >25 | >25 | >25 | >25 | >25 |
| Product of Example VI | 10.8 | >25 | >25 | >25 | >25 | >25 |
| Product of Example VII | 11.1 | >25 | >25 | >25 | >25 | >25 |
| Product of Example VIII | 15.6 | >25 | >25 | >25 | >25 | >25 |

*The hardness of the samples at various compression pressures is measured by a Strong Cobb Hardness meter and is compared with those of conventional tablets.

Note:
The maximum pressure used in forming the tablets is usually 2000 kg/cm², and the tablets preferably should have a hardness of at least 5. The desired hardness of the tablets should preferably be obtained with as low a compression pressure as possible. That is, it is seen from the above table that the numerical values given under "Crystallized cellulose", and those samples which follow, can be regarded as being desirable numerical values.

EXAMPLE I

A mixed aqueous solution of 0.6 m/l of magnesium nitrate and 0.2 M/l of aluminum nitrate, an alcohol solution of 0.05 M/l of salicylsalicylic acid, and a 50 % alcohol solution of 0.5 M/l of sodium hydroxide are prepared.

These three solutions are put into a 0.6 -liter reaction tank equipped with an overflow apparatus using a metering pump so that the flow rates of the mixed solution of magnesium nitrate and aluminum nitrate, the alcohol solution of salicylsalicylic acid and the 50 % alcohol solution of sodium hydroxide are 3.2 ml per minute, 19.4 ml per minute and about 12 ml per minute, respectively. In this case, the reaction tank is filled in advance with 200 ml of a 50 % alcohol solution, and the flow rate of the 50 % alcohol solution of sodium hydroxide is adjusted so as to maintain the pH of the reaction solution at 10.0 – 10.5.

The liquid which overflows during the period up to one hour after the start of the reaction is discarded, and the reaction suspension overflowing thereafter is collected. The foregoing reaction is carried out in a stream of nitrogen.

The reaction suspension has the water removed, and is washed and dried at 70°C, to obtain the intended product having the chemical composition:

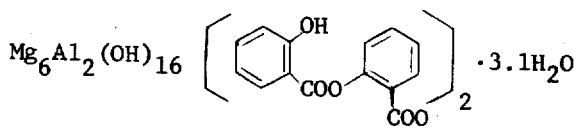

and an X-ray diffraction analysis:

| dA | 8.23 | 4.12 | 2.70 |
|---|---|---|---|
| hkl | 003 | 006 | 102 |

EXAMPLE II

Water, which has had the carbonic acid removed, is used, and an aqueous solution in 200 ml of water of 4.8 grams of $AlCl_3 \cdot 6H_2O$ and 12.2 grams of $MgCl_2 \cdot 6H_2O$, and an aqueous solution in 100 ml of 0.5N aqueous NaOH solution of 7.5 grams of chinophenum are prepared.

The aqueous NaOH solution of chinophenum is placed in a 4-neck round bottom flask, and electrodes of a pH meter are inserted into the flask.

While maintaining a carbon dioxide free state in the flask by passing air having the carbon dioxide removed therethrough, the foregoing two remaining solutions are each added dropwise by means of a buret while stirring the reaction solution and maintaining the temperature of the solution at 25°C., the amount of the two solutions added being adjusted so that the reaction solution is maintained at a pH of 10.0 – 10.5.

After completion of the dropwise addition, the reaction solution is stirred for about 10 minutes, following which the reaction suspension is withdrawn. The reaction suspension is then filtered under reduced pressure, and the resulting reaction product is washed with 200 ml of ion-exchanged water and dried for 15 hours at 75°C. with a through-circulation dryer to thus obtain the intended product having the chemical composition:

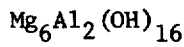

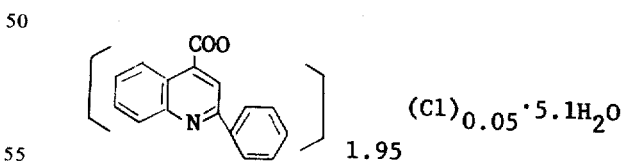

and an X-ray diffraction analysis:

| dA | 8.31 | 4.17 | 2.67 |
|---|---|---|---|
| hkl | 003 | 006 | 102 |

EXAMPLE III

Carbon dioxide free water is used to prepare an aqueous solution of 2 mols per liter of NaOH, an aqueous solution in 200 ml of water of 4.8 grams of $AlCl_3 \cdot 6H_2O$ and 12.2 grams of $MgCl_2 \cdot 6H_2O$, and a solution in 100 ml of ethanol of 5.8 grams of p-isobutylphenylacetic acid (Ibufenac).

A 4-neck round bottom flask is charged with the alcohol solution of Ibufenac, and electrodes of a pH meter are inserted into the flask.

While excluding the carbon dioxide from the flask by passing carbon dioxide free air therethrough, the foregoing two remaining solutions are each added dropwise by means of a buret while stirring the reaction solution and maintaining the temperature of the solution at 25°C., the amount of the two solutions added being adjusted so that the reaction solution is maintained at a pH of 10.0 – 10.5.

After completion of the addition of the solutions, the stirring is continued for a further 10 minutes. The resulting reaction suspension is then withdrawn and the water is removed under reduced pressure. The resulting reaction product is then washed with 200 ml of ion-exchanged water and dried for 15 hours at 75°C. with a through-circulation dryer. The product which was obtained has the chemical composition:

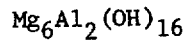

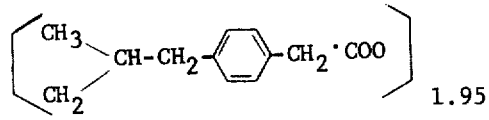

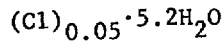

and an X-ray diffraction analysis:

| dA | 8.18 | 4.08 | 2.70 |
|---|---|---|---|
| hkl | 003 | 006 | 102 |

EXAMPLE IV

Carbon dioxide free water is used to prepare an aqueous solution of 2 mols per liter of NaOH, an aqueous solution in 200 ml of 4.8 grams of $AlCl_3 \cdot 6H_2O$ and 12.2 grams of $MgCl_2 \cdot 6H_2O$, and an aqueous solution in 100 ml of water of 2.5 grams of sodium salicylate.

A 4-neck round bottom flask is charged with the aqueous sodium salicylate solution, and electrodes of a pH meter are inserted into the flask.

While excluding the carbon dioxide from the flask by passing carbon dioxide free air therethrough, the foregoing two remaining solutions are each added dropwise by means of a buret while stirring the reaction solution and maintaining the temperature of the solution at 25°C., the amount of the two solutions added being adjusted so that the reaction solution is maintained at a pH of 13 or above.

After completion of the addition of the solutions, the stirring is continued for a further 10 minutes, following which the resulting reaction suspension is withdrawn and its water is removed under reduced pressure. Fifty ml of a 3 % aqueous sodium salicylate solution is then poured over the resulting reaction product after which it is washed with 100 ml of ion-exchanged water and dried for 15 hours at 75°C. with a through-circulation dryer. Thus, the intended product is obtained having the chemical composition:

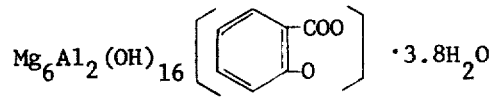

and X-ray diffraction analysis:

| dA | 7.96 | 3.93 | 2.61 |
|---|---|---|---|
| hkl | 003 | 006 | 102 |

Figure 2:
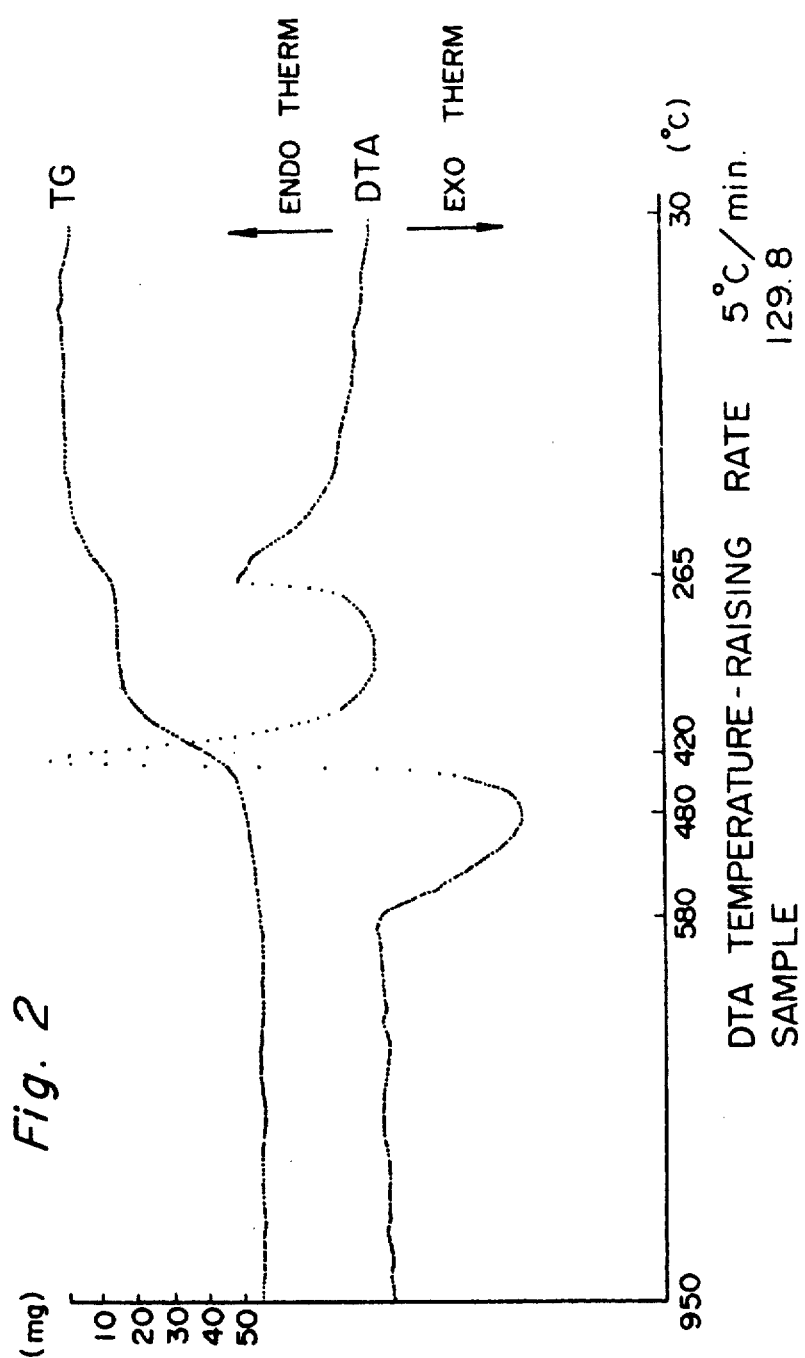
Figure 3:
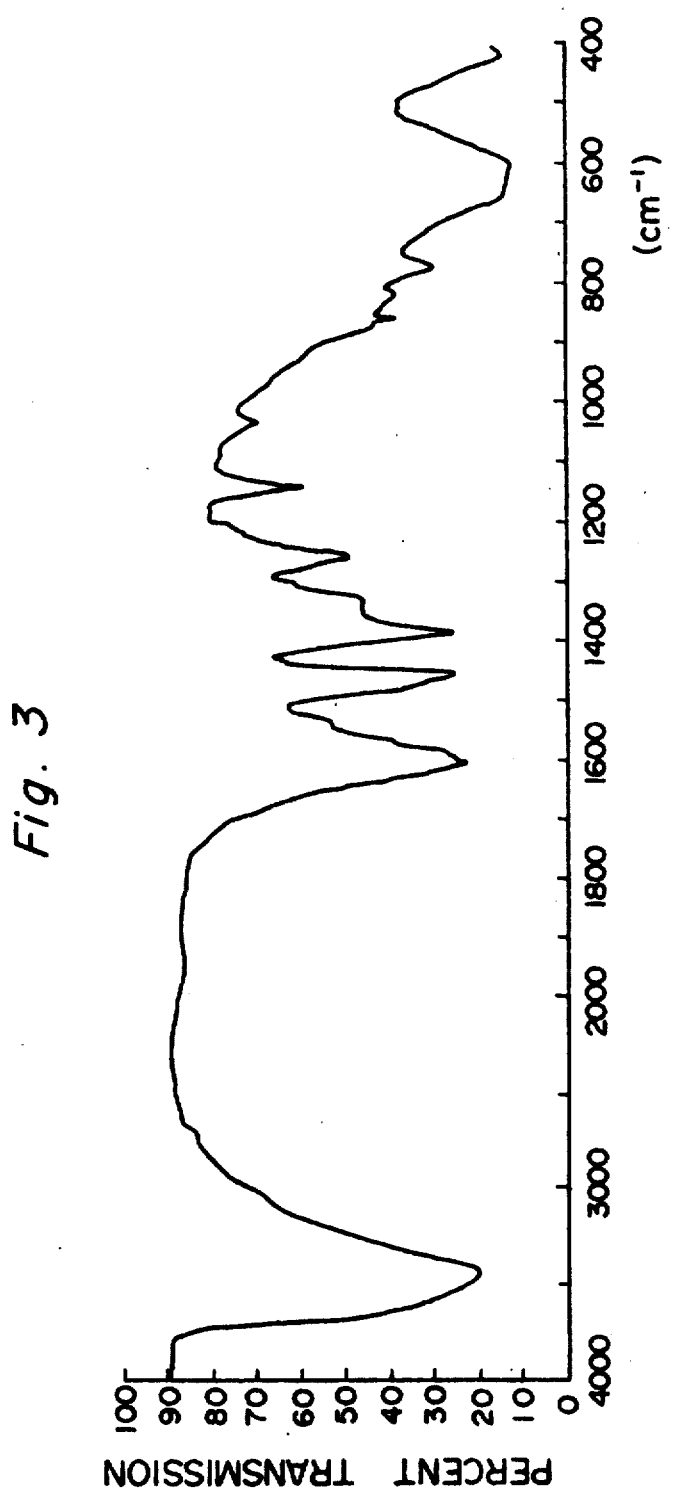

See FIG. 1 for the X-ray diffraction pattern, FIG. 2 for the differential thermal analysis, FIG. 3 for the infrared absorption analysis and FIG. 4 for the pH curve as determined by the Fuch's method.

The Fuch's method will be described below.

Although the Holbert et al. test method was adopted for appreciating the antacid activity in the Schenck et al. reference, Fuch's modification test method, which is a highly improved test method over the Holbert et al. method, was adopted in these experiments.

Fuch's modification test method is a method for measuring the antacid in vitro employing a model stomach.

The following two artificial gastric juices were used in tests.

| *Artificial gastric juice A: | |
|---|---|
| Table salt (high quality) | 2.0 grams |
| Diluted hydrochloric acid | 24.0 ml |
| Distilled water | balance |
| Total | 1000 ml |
| | (0.068 N) |
| *Artificial gastric juice B: | |
| Table salt (high quality) | 2.0 grams |
| Concentrated pepsin | 2.1 grams |
| (1 : 5000) | |
| (Product of Mikuni Chemical Co.) | |
| Diluted hydrochloric acid | 24.0 ml |
| Distilled water | balance |
| Total | 1000 ml |
| | (0.068 N) |

The test operation was conducted in the following manner:

150 ml of artificial gastric juice was charged in a 500-ml beaker, which was then fixed on a magnetic stirrer and dipped into a thermostat maintained at 37.5°C. Electrodes of a pH meter and a thermometer were inserted into the beaker. Then the content of the beaker was stirred by means of the magnetic stirrer. When the temperature of the content of the beaker reached 37.5°C., 1 gram of the sample was added thereto and simultaneously a chart-recorder was operated. After 10 minutes had passed, a constant-volume pump was actuated and the addition of the gastric juice at a rate of 2 ml/min was commenced.

The values of the following antacid characteristics were measured from the recorded chart:

Rapidity: Time required for the gastric juice to reach a pH of 3.0.

Maximum pH: Maximum pH value observed in the measurement.

Duration: Time required for the gastric juice to reach a pH below 3.0.

Reactivity with acid: The ratio of the amount consumed of gastric juice actually measured to the amount consumed of gastric juice calculated from the value of acid consuming capacity.

EXAMPLE V

Carbon dioxide free water is used to prepare an aqueous solution of 2 mols per liter of NaOH, an aqueous solution in 200 ml of water of 4.8 grams of $AlCl_3 \cdot 6H_2O$ and 12.2 grams of $MgCl_2 \cdot 6H_2O$, and an aqueous solution in 100 ml of water of 4.8 grams of sodium salicylate.

A 4-neck round bottom flask is charged with the aqueous sodium salicylate solution, and the electrodes of a pH water are inserted in the flask.

While excluding the carbon dioxide from the flask by passing carbon dioxide free air therethrough, the foregoing two remaining solutions are each added dropwise by means of a buret while stirring the reaction solution and maintaining its temperature at 25°C., the amount added of the two solutions being adjusted so that the reaction solution is maintained at a pH of 10.0 – 10.5.

After completion of the addition, the stirring is continued for about 10 minutes, following which the resulting reaction suspension is withdrawn from the flask and its water is removed under reduced pressure. The reaction product thus obtained is washed with 70 ml of ion-exchanged water, following which 200 ml of a 3 % aqueous sodium salicylate solution is poured over the reaction product, and thereafter the product is water-washed, followed by drying for 15 hours at 75°C. in a through-circulation drier to obtain the intended product having the chemical composition:

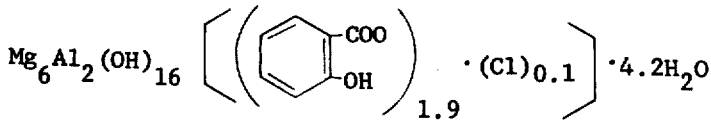

and X-ray diffraction analysis:

| dA | 7.69 | 5.30 | 3.97 |
|---|---|---|---|
| hkl | 003 | 006 | 102 |

EXAMPLE VI

Using 75 % ethanol and isopropanol, 200 ml of a mixed solution of 0.6 M/liter of magnesium nitrate and 0.2 M/liter of aluminum isopropoxide and 400 ml of an ethanol solution of 0.2 M/liter of Indomethacin are prepared. A 4-neck 1-liter flask is charged with the ethanol solution of Indomethacin, and electrodes of a pH meter are inserted in the flask. While stirring the contents of the flask with a magnetic stirrer, the foregoing mixed solution and ammonia gas are added at room temperature and normal atmospheric pressure, the addition being made in such a manner that the reaction solution is maintained at a pH of 8.0 ± 0.5. After completion of the reaction, the resulting reaction suspension is filtered under reduced pressure, washed in ethanol, followed by washing with ion-exchanged water and thereafter drying to obtain the intended product. This product checks gastric disorders and ill effects produced by the use of Indomethacin (an antiphlogistic). Furthermore, an effective and excellent antiphlogistic effect is had by the use of this product even in minute dosages. The reaction and the other steps of this experiment were carried out in an atmosphere of nitrogen.

Chemical composition:

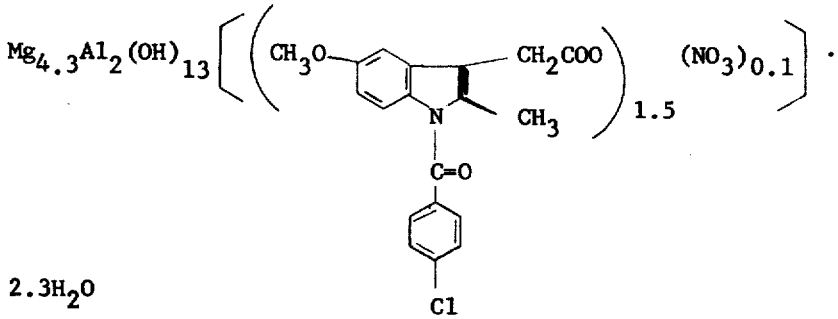

X-ray diffraction analysis:

| dA | 8.66 | 4.32 | 2.88 |
|---|---|---|---|
| hkl | 003 | 006 | 102 |

See FIGS. 5 and 6 for the infrared absorption analysis.

EXAMPLE VII

A mixed aqueous solution of 0.6 M/liter of magnesium nitrate and 0.1 M/liter of aluminum nitrate, an aqueous solution of 0.1 M/liter of flufenamic acid (the flufenamic acid dissolved in water after addition of a dilute aqueous solution of sodium hydroxide), and an aqueous solution of 0.5 M/liter of sodium hydroxide are prepared. These three solutions are put into an overflow apparatus-equipped 0.6 liter reaction tank at the flow rates of 3.2 ml per minute for the mixed solution of the magnesium and aluminum salts, 9.7 ml per minute for the aqueous flufenamic acid solution and 10.3 ml per minute for the aqueous sodium hydroxide solution, using a metering pump. Prior to the foregoing additions, the reaction tank is filled with 200 ml of water which is constantly stirred by agitation with a constant speed agitator. Electrodes of a pH meter are also kept submerged in the water. The flow rate of the aqueous sodium hydroxide solution is adjusted so as to maintain the reaction solution constantly at a pH of 10.0 – 10.5. The reaction is carried out for 4 hours. The liquid overflowing during the first hour of the reaction is discarded, but the reaction suspension overflowing thereafter is regarded as being stable and hence is collected in a vessel. The collected reaction suspension is dehydrated under reduced pressure, washed in water and thereafter dried at 70°C. to obtain the intended product. This product checks gastric disorders and ill effects produced by the use of flufenamic acid (an antiphlogistic). Moreover, it has an effective and excellent antiphlogistic effect even though it is used in minute dosages. This reaction was conducted in an atmosphere free of carbonic acid.

Chemical composition:

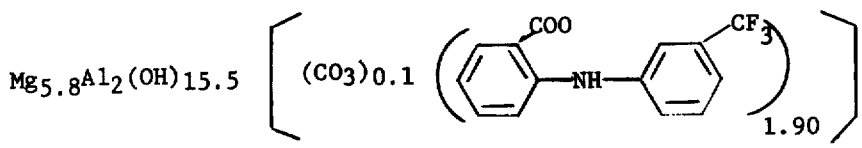

X-ray diffraction analysis:

| dA | 7.62 | 4.07 | 2.59 |
|---|---|---|---|
| hkl | 003 | 006 | 102 |

Figure 7:
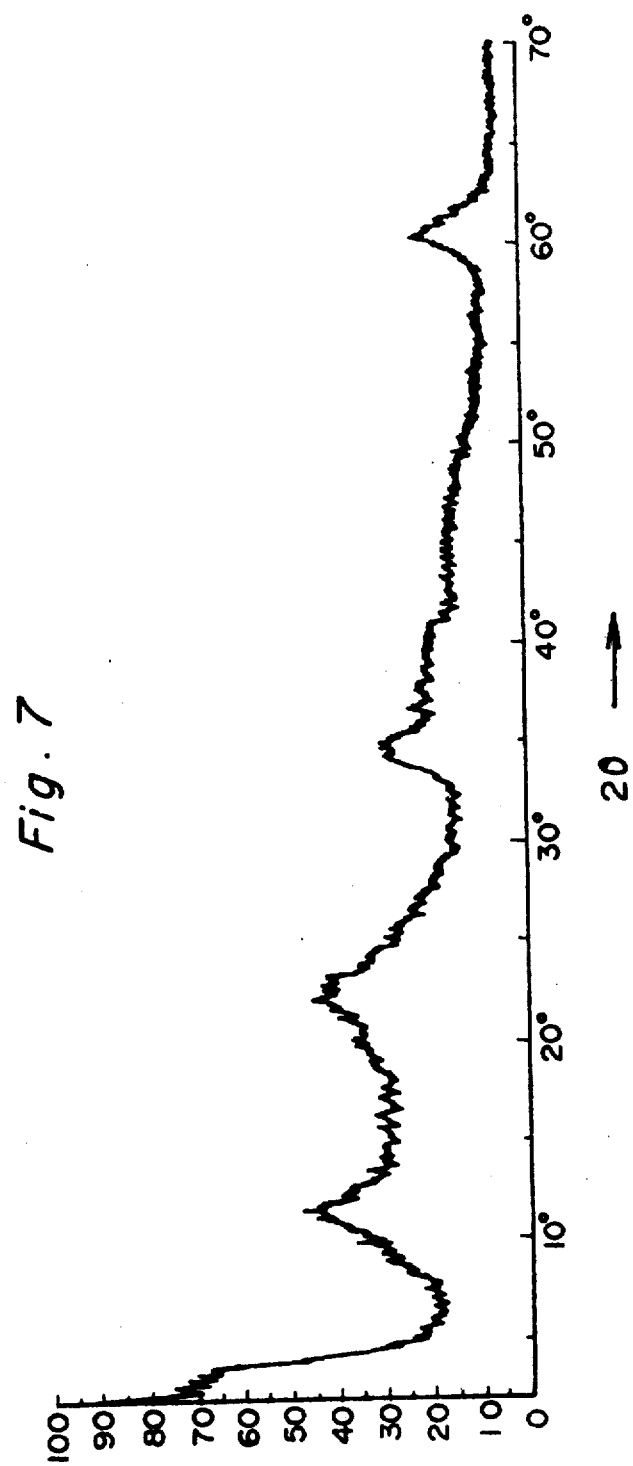
Figure 8:
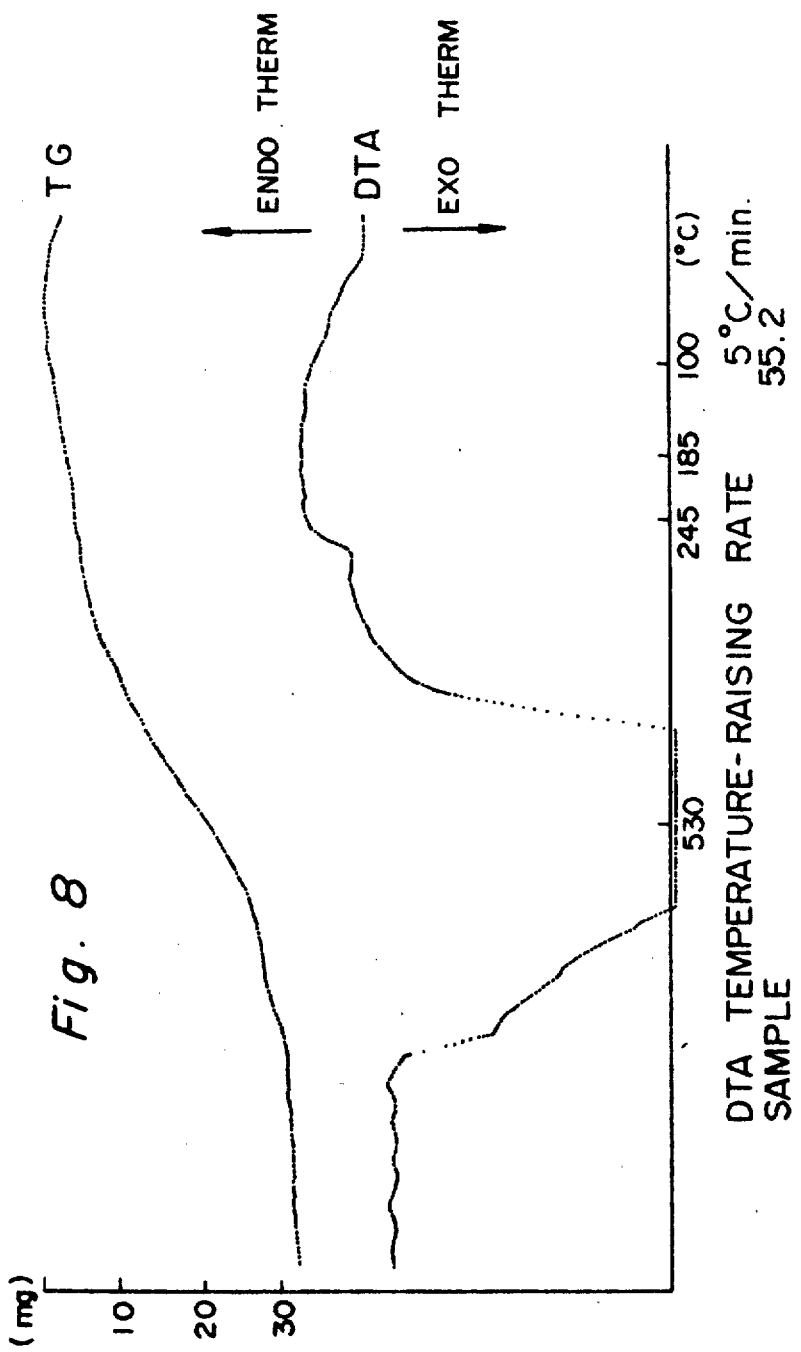
Figure 9:
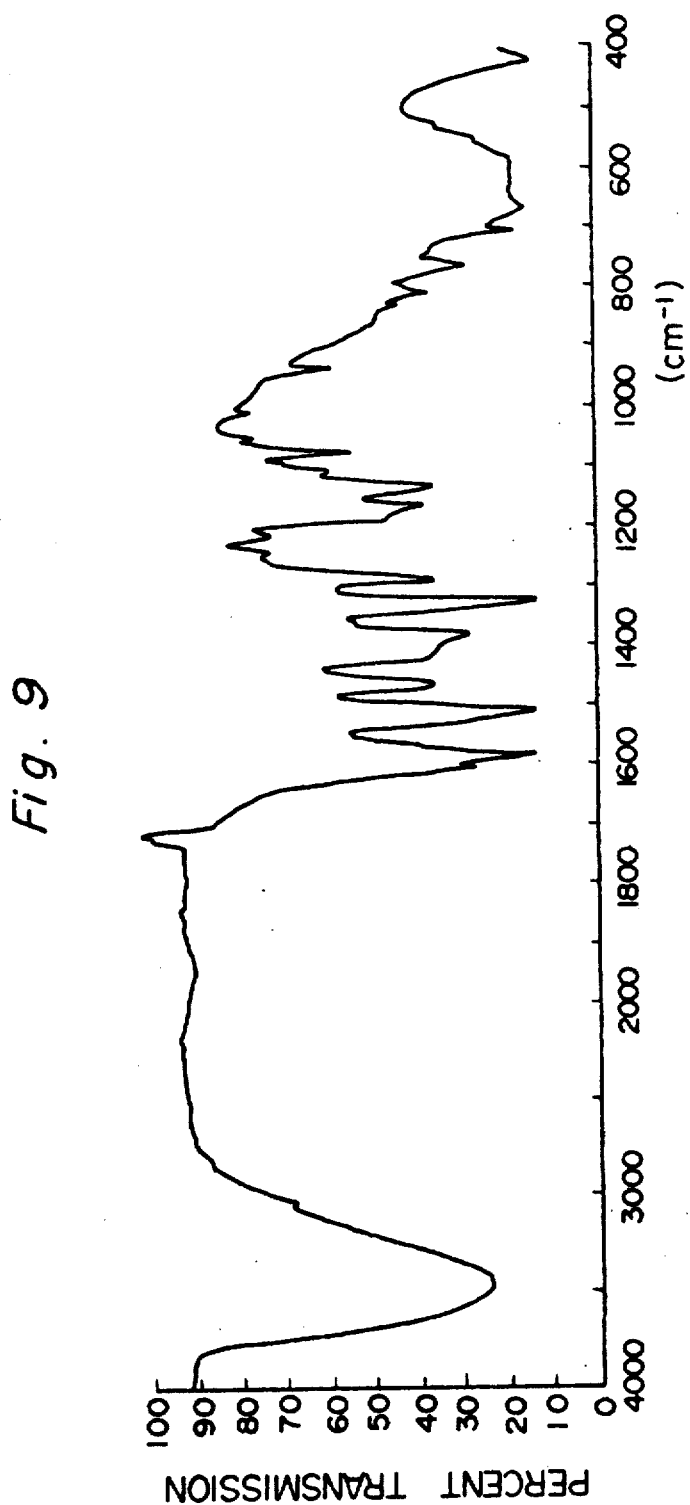

See FIGS. 7, 8 and 9 respectively for the X-ray analysis, differential thermal analysis and infrared analysis.

EXAMPLE VIII 200 ml of a mixed aqueous solution of 0.8 M/liter of magnesium chloride and 0.2 M/liter of sodium aluminate, 125 ml of a 50 % ethanol solution of 0.4 M/liter of p-isobutyl hydrotropic acid (Ibuprofen), and an aqueous solution of 2 M/liter sodium hydroxide solution are reacted by adding dropwise each of the foregoing solutions from three burets into a magnetic stirrer-agitated 1-liter beaker which has electrodes of a pH meter submerged therein. All the water used in this reaction is ion-exchanged water. The reaction is conducted in a stream of nitrogen and by dropping the foregoing solutions at flow rates so as to maintain the reaction solution at a pH of 10.0 – 10.5. After completion of the reaction, the resulting precipitate is filtered under reduced pressure, followed by washing in ion-exchanged water and drying at 80°C.

Chemical composition:

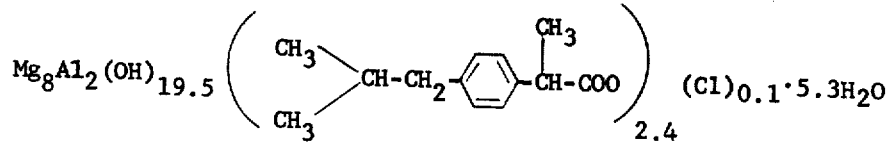

X-ray diffraction analysis:

| dA | 8.12 | 4.06 | 2.69 |
|---|---|---|---|
| hkl | 003 | 006 | 102 |

What is claimed is:
1. A compound having a composition of the formula

$$Mg_xAl_y(OH)_{2x+3y-z}(A)_z \cdot aROH$$

wherein A is a member selected from a mono- or bivalent anion of a compound of the formula

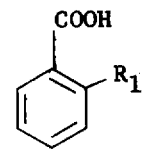

wherein $R_1$ is a member selected from the group consisting of hydroxyl, acetyloxy, salicyloxy, 3-trifluoromethylphenylamino and 2,3-dimethylphenylamino; and a combination of said mono- or bivalent anion of the compound and not more than 50 mol %, based on the total anions, of an ion selected from the group consisting of halogen, nitrate, carbonate and sulfate ions, R is a member of the group consisting of hydrogen and ethyl, and $x$, $y$, $z$ and $a$ are each a positive number satisfying the following relationships:

$x$ is a number from 3 to 10 when $y$ is 2;
$z$ is a number from 1.5 to 2.5 when A is a monovalent anion, and from 0.75 to 1.25 when A is a bivalent anion; and
$a$ is a number from 2.5 to 6;

said compound having an X-ray diffraction pattern substantially identical to that indicated below:

| dA | hkl |
|---|---|
| 7.62 ~ 21.02 | 003 |
| 3.93 ~ 9.40 | 006 |
| 2.11 ~ 6.91 | 102 |
| 2.34 ± 0.5 | 105 |
| 2.00 ± 0.5 | 108 |
| 1.53 ± 0.05 | 110 |
| 1.50 ± 0.05 | 113 |

2. The compound of claim 1 wherein A is an anion of a compound of formula

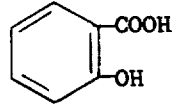

and has the chemical composition formula:
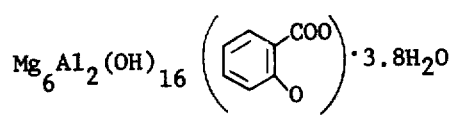
3. The compound of claim 1 wherein A is an anion of a compound of the formula
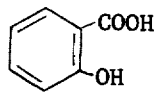
and has the chemical composition formula:
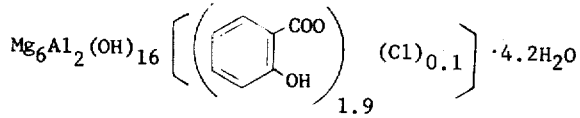
4. The compound of claim 1 wherein A is an anion of a compound of the formula
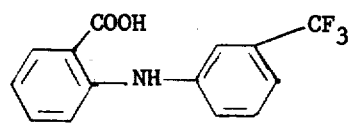
and has the chemical composition formula:
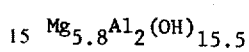
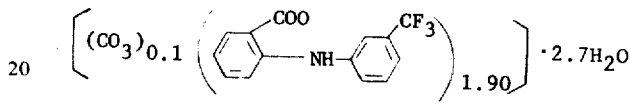
* * * * *